PROCESS FOR THE PREPARATION OF 4-ETHOXYPHENYL-3-ARYLPROPYL(DIMETHYL)SILANES

[75] Inventor: Harald Knorr, Frankfurt am Main, Fed. Rep. of Germany

[73] Assignee: Hoechst Aktiengesellschaft, Frankfurt am Main, Fed. Rep. of Germany

[21] Appl. No.: 766,855

[22] Filed: Sep. 27, 1991

[30] Foreign Application Priority Data

Oct. 1, 1990 [DE] Fed. Rep. of Germany ....... 4031001

[51] Int. Cl.$^5$ ............................................. C07F 7/08
[52] U.S. Cl. ................................... 556/445; 556/427; 556/479
[58] Field of Search ..................... 556/479, 427, 445

[56] References Cited

U.S. PATENT DOCUMENTS

| | | | |
|---|---|---|---|
| 2,823,218 | 2/1958 | Speier et al. | 556/479 X |
| 4,226,426 | 6/1981 | Lindner et al. | 556/479 |
| 4,454,331 | 6/1984 | Zeller et al. | 556/479 X |
| 4,537,983 | 8/1985 | Seiler et al. | 556/479 |
| 4,898,961 | 2/1990 | Baile et al. | 556/479 |

*Primary Examiner*—Paul F. Shaver
*Attorney, Agent, or Firm*—Curtis, Morris & Safford

[57] ABSTRACT

The present invention relates to a process for the preparation of compounds of the formula I

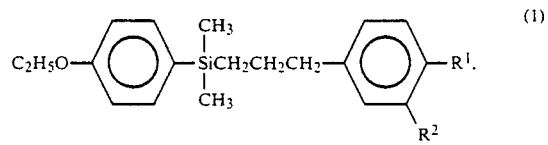

in which
$R^1$ is hydrogen, halogen, alkyl, alkoxy and
$R^2$ is hydrogen, halogen, alkoxy or phenoxy, which may be substituted by halogen, alkyl, alkoxy or alkylthio, by reaction of a compound of the formula II

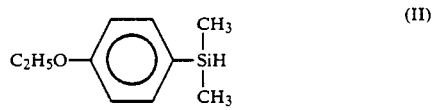

with a compound of the formula II

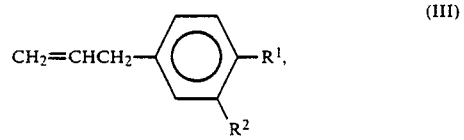

in which $R^1$ and $R^2$ have the meanings as in formula I, in the presence of catalytically active amounts of hexachloroplatinic acid, which comprises metering the starting compounds of the formulae II and III simultaneously into the reaction vessel at temperatures of 60° C. to 150° C. and allowing the reaction to go to completion.

3 Claims, No Drawings

PROCESS FOR THE PREPARATION OF 4-ETHOXYPHENYL-3-ARYLPROPYL(DIMETHYL)SILANES

DESCRIPTION

The present invention relates to a process for the preparation of compounds of the formula I

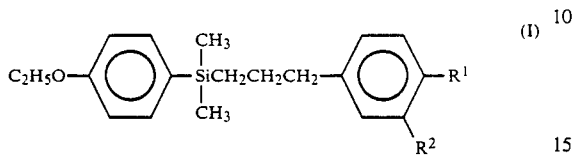

in which
$R^1$ is hydrogen, halogen, ($C_1$-$C_4$)alkyl, ($C_1$-$C_4$)alkoxy and
$R^2$ is hydrogen, halogen, ($C_1$-$C_4$)alkoxy or phenoxy, which may be substituted by halogen, ($C_1$-$C_4$)alkyl, ($C_1$-$C_4$)alkoxy or ($C_1$-$C_4$)alkylthio, by reaction of a compound of the formula II

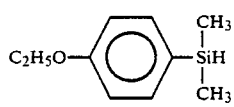

with a compound of the formula III

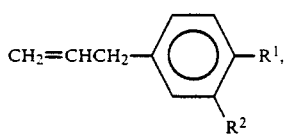

in which $R^1$ and $R^2$ have the meanings as in formula I, in the presence of catalytically active amounts of hexachloroplatinic acid, which comprises metering the starting compounds of the formulae II and III simultaneously into the reaction vessel at temperatures of 60° C. to 150° C. and allowing the reaction to go to completion.

The preferred temperature range in this reaction is 80°-130° C. A further particular embodiment of the process according to the invention consists in adding the hexachloroplatinic acid which acts as a catalyst to the allylbenzene of the formula III and metering this mixture simultaneously with a compound of the formula II into the reaction vessel.

4-Ethoxyphenyl-3-arylpropyl(dimethyl)silanes serve as valuable intermediates in the preparation of insecticides or have themselves insecticidal effects (EP-A 0,224,024).

The 4-ethoxyphenyl-3-arylpropyl(dimethyl)silanes I are prepared by hydrosilylation of allylbenzenes of the formula III with 4-ethoxyphenyl(dimethyl)silane of the formula II, it being possible to carry out the reaction in the presence of catalytic amounts of hexachloroplatinic acid.

The general procedure of hydrosilylation is such that the components undergoing the addition reaction are initially introduced and the catalyst is then added, as a result of which the reaction is initiated after an induction phase. When the process is carried out in this manner, very large amounts of heat are liberated within a short time, which may lead to dangerous situations especially when preparing fairly large amounts (J. L. Speier: "Homogeneous Catalysis of Hydrosilation by Transition Metals", Adv. Organom. Chem. Vol. 17 (409) 1979). Unwanted side reactions take place in this procedure, leading to significant reductions in yield.

Thus, about 14-20% of "styrenes" of the formula A

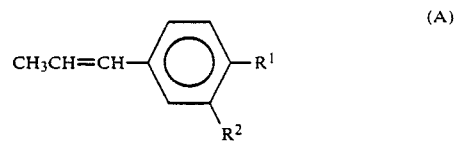

are found. These compounds obstruct the formation of the desired 4-ethoxyphenyl-3-arylpropyl(dimethyl)silanes insofar as they react further with the silanes of the formula II to give isomeric 4-ethoxyphenyl-2-arylethyl(dimethyl)silanes of the formula B

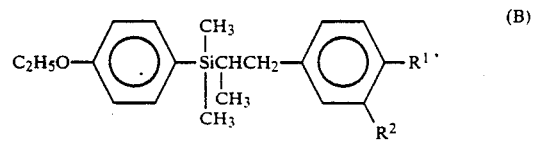

The final product must therefore be separated off from undesirable components by distillation.

A process in which silanes are reacted with olefins in the presence of a complex compound of an element from subgroup VIII of the periodic table as a catalyst is also known (EP-A 0,224,024). This reaction is carried out at moderate temperatures (about 45° C.) without solvent (cf. also Houben Weyl, Methoden der organischen Chemie (Methods of organic chemistry), Vol. XIII/5, Georg Thieme Verlag, Stuttgart 1980, p. 51 ff).

Surprisingly, a very simple process for the preparation of 4-ethoxyphenyl-3-arylpropyl(dimethyl)silanes of the formula I has now been found by which the side reactions described above can be circumvented and by which in addition it is simpler to obtain the product. Thus, if the starting components undergoing the addition reaction are combined simultaneously, the otherwise strong exothermic reaction proceeds in a moderate way. This procedure makes it possible in a simple manner to significantly increase the yields of the desired 4-ethoxyph-enyl-3-arylpropyl(dimethyl)silanes.

It was not foreseeable that this special method of addition would be successful and that it would be possible in a simple manner to prepare the desired 4-ethoxyphenyl-3-arylpropyl(dimethyl)silanes. Thus, if one of the two starting components is added to the other, the strongly exothermic reaction already described at the beginning, in which temperatures of more than 140° C. may occur, is likewise observed. However, this leads to losses in the yield and to maximum isolatable amounts of the product of only about 85-86% of theory.

The starting materials of the formulae II and III necessary for the process according to the invention are either known (EP-A 0,224,024) or can be prepared like the precursors necessary for their preparation very similarly to reactions known from the literature: A. Citterio, Org. Synth. 62, 67 (1984); E. Möller, R. Schöter, Methoden der org. Chemie (Methods of organic chemistry) (Houben-Weyl) Vol. XI/71, 648–664, (1957); A. C. Cope, C. L. Bumgardner, J. Amer. Chem. Soc. 79, 960 (1957)); see Methoden der org. Chemie (Methods of organic chemistry) (Houben-Weyl), Vol. XIII/5, Georg Thieme Verlag, Stuttgart 1980; E. Pfeil, Angew. Chem. 65, 155-158 (1953); H. H. Hodgson, Chem. Rev. 40, 251-277 (1947); H. Fricke, Methoden der org. Chemie (Methods of organic chemistry) (Houben-Weyl), Vol. V/lb, 465-476 (1972).

The allylbenzenes of the formula II used in the process according to the invention are in particular 4-fluoro-3-phenoxyallylbenzene and 4-fluoro-3-chloroallylbenzene and 4-fluoro-3-bromoallylbenzene, in most cases equimolar amounts being preferred, relative to the silane of the formula II. However, it is also possible to use one of the possible starting materials in an excess of up to 20 mol %.

It is also advantageous to use the products of the process according to the invention of the formula I themselves as solvent or initially to introduce them before the reaction starts. This last-mentioned measure is sensible in particular if the reaction is to be conducted continuously. The reaction temperature during the reaction varies between 60° C. and 150° C. However, the reaction is particularly advantageously carried out between 80° C. and 130° C.

The catalyst used is hexachloroplatinic acid, which, as is known, is used for hydrosilylation. Amounts between 0.5 mg and 50 mg of $H_2PtCl_6 \times 6\ H_2O$ are used per mol of educt of the formula III, in most cases in the form of a 30% solution in isopropanol.

For improved metering, it is advantageous to dissolve the catalyst in one of the two starting materials of the formulae II or III. It is advantageous if the catalyst is present in dissolved form in the starting compound of the formula III.

The reaction is preferably carried out without the presence of solvents or, alternatively, in the presence of compounds of the formula I. However, it is also possible to use other solvents, such as hydrocarbons, halogenated hydrocarbons, ethers and aromatics and halo aromatics, if they boil between 60° C. and 140° C.

The process according to the invention can be carried out such that, for example, first the catalyst is dissolved in the allylbenzene of the formula III and this solution is metered simultaneously with the silane of the formula II into a reaction vessel, containing a small amount of the product of the formula I, at about 100° C. The reaction is allowed to go to completion, and the product formed of the formula I is advantageously removed after a phase of additional stirring.

The product can be isolated from the reaction mixture by distillation, in which first a small amount of low-boiling components are removed. Owing to the complete reaction when the procedure according to the invention is employed, it is also possible to remove the catalyst together with the water and then to make the product available for any further reactions in undistilled form.

The process according to the invention is illustrated by the examples which follow.

EXEMPLARY EMBODIMENTS

Example 1

4-ethoxyphenyl-3-(4-fluoro-3-chlorophenyl)propyl(-dimethyl)silane 1 drop of hexachloroplatinic acid (30% in isopropanol) is added to 0.3 mol of 4-fluoro-3-chloroallylbenzene (51.6 g, 99.2% pure). This solution is added dropwise simultaneously with 0.3 mol of 4-ethoxyphenyl(-dimethyl)silane (56 g, 96.5% pure) to a stirred flask at a starting temperature of 95° C. over a period of 40 minutes. The internal temperature is maintained at about 100° C. Stirring at 100° C. is continued for 1 hour, to give, according to GC, a mixture of 0.8% of 4-fluoro-3-chloroallylbenzene (=1.7% of theory), 0.8% of 4-ethoxyphenyl(dimethyl)silane (=1.6% of theory), 94.7% of 4-ethoxyphenyl-3-[4-fluoro-3-chlorophenyl]-propyl(dimethyl)silane (=96.6% of theory).

Example 2

(Comparative example)

5.564 mol (1042 g, 96.1% pure) of 4-ethoxyphenyl(-dimethyl)silane are initially introduced at 100° C. 5.617 mol (1000 g, 95.9 % pure) 4-fluoro-3-chloroallylbenzene plus 12 drops of 30% $H_2PtCl_6$/isopropanol solution are added dropwise over a period of 47 minutes. During this time, the temperature rises to 143° C. During the dropwise addition, the temperature is maintained at about 134°-137° C. and, after the reaction is complete, 285.3 g of product are distilled off in a high vacuum of 0.1 mbar at a column head temperature of 47°-160° C. About 1732 g (96.9% pure) of the product then distil over between 160°-170° C. and at 0.1-0.05 mbar. This corresponds to a yield of 85-86% of theory.

Example 3

(Comparative example)

3 drops of a 30% solution of hexachloroplatinic acid in isopropanol are added at room temperature to a mixture of 1.37 mol (234 g, 99.9% pure) of 4-fluoro-3-chloroallylbenzene and 1.45 mol (263 g, 99.2% pure) of 4-ethoxyphenyl(dimethyl)silane. After a short induction phase, a strong exothermic reaction takes place and the mixture heats to 130° C. Stirring of the mixture is continued for a short time, and 392 g of 4-ethoxyphenyl-3-(4-fluoro-3-chlorophenyl)propyl(dimethyl)silane are then distilled off as the main fraction at 165°-170° C. and 0.1 mbar. This corresponds to a crude yield of 81.6% (97.4% pure by GC, 79.5 % of theory).

Example 4

4-ethoxyphenyl-3-(4-fluoro-3-phenoxyphenyl)propyl(-dimethyl)silane (Comparative example)

A few drops of a 30% solution of hexachloroplatinic acid in isopropanol are added twice at 22° C. to a mixture of 2.98 mol of 4-fluoro-3-phenoxyphenylallylbenzene (98.9% pure, 687 g) and 3.24 mol of 4-ethoxyphenyl(dimethyl)silane (595 g, 97.9% pure). After an induction phase of 1½ hours, spontaneous heating to 130° C. takes place. After stirring is continued for a short period, 259 g of forerun are distilled off in a high vacuum of 0.4-0.15 mbar, followed by 1003 g of product (98.7% pure by GC). This corresponds to a yield of 81.4% of theory.

Example 5

4-ethoxy-3-(4-fluoro-3-phenoxyphenyl)propyl(dimethyl)silane 10 drops of a 30% solution of $H_2PtCl_6$ in isopropanol are added to 2.98 mol of 4-fluoro-3-phenoxyphenylallylbenzene (98.9% pure, 687 g). This solution is added dropwise simultaneously with 3.0 mol of 4-ethoxyphenyl(dimethyl)silane (552 g, 97.9% pure) to a stirred flask at 100° C. over a period of 1½ hours while being maintained at 100° C. Stirring is continued for 1 hour, to give a crude mixture (1240 g) having a composition of 95.1% of 4-ethoxyphenyl-3-(4-fluoro-3-phenoxyphenyl)propyl(dimethyl)silane (=97% of theory), 1.0% of 4-ethoxyphenyl(dimethyl)silane (=1.6% of theory), 0.9% of 4-fluoro-3-phenoxyphenylallylbenzene (=1.7% of theory). If this mixture is distilled in a molecular evaporator, 1177 g of a 99% pure product are obtained. This corresponds to a yield of 95.8% of theory.

Example 6

(Comparative example) (analogously to Example 2)

5.29 mol of 4-ethoxyphenyldimethylsilane (978 g, 97.3% pure) were initially introduced at 110° C. A mixture of 5.2 mol of 4-fluoro-3-chloroallylbenzene (928 g, 95.5% pure) and 11 drops of a 30% $H_2PtCl_6$/isopropanol solution was added dropwise over a period of 40 minutes. An increase in temperature to 158° C. takes place. After distillation in a high vacuum at 160°–165° C. and 0.1 mbar, 1481.3 g (97% pure) of 4-ethoxyphenyl-3-(4-fluoro-3-chlorophenyl)propyldimethylsilane were obtained. This corresponds to a yield of 78.8% of theory.

Example 7

(Comparative example) (analogously to Example 2)

0.145 mol of 4-ethoxyphenyldimethylsilane (26.6 g, 98.1% pure) was initially introduced at 25° C. A mixture of 23.4 g of 4-fluoro-3-chloroallylbenzene (0.14 mol, GC:99.8%) and 3 drops of a 30% $H_2PtCl_6$/isopropanol solution was metered in at 25° C. over a period of 30 minutes. An exothermic reaction sets in and the internal temperature rapidly rises to 122° C. After distillation in a high vacuum at 160°–165° C. and 0.1 mbar, 40.1 g (92.7% pure) of product remain. This corresponds to a yield of 77.4% of theory.

Example 8

(Comparative example)

3 drops of a 30% $H_2PtCl_6$/isopropanol solution are added to 0.3 mol (56.2 g, 96% pure) of 4-ethoxyphenylsilane at room temperature. 0.3 mol (51.6 g, 99% pure) of 4-fluoro-3-chloroallylbenzene are initially introduced at 100° C., and the above mixture is added over a period of 30 minutes. This results in an exothermal increase to 140° C. 88.7 g (96% pure) of 4-ethoxyphenyl-3-(4-fluoro-3-chlorophenyl)propyldimethylsilane are then distilled off in a high vacuum at 160°–162° C. and 0.05 mbar. This corresponds to a yield of 81.0 % of theory.

The following examples were carried out analogously:

| Comparative Examples | Initial temperature °C. | Exothermal increase to [°C.] | Product yield % of theory |
|---|---|---|---|
| 9 | 20 | 131 | 79.8 |
| 10 | 70–80 | 129 | 82.6 |

Example 11

(Comparative example)

0.14 mol (23.4 g) of 4-fluoro-3-chloroallylbenzene and 3 drops of a 30% $H_2PtCl_6$/isopropanol solution were initially introduced at room temperature. 0.145 mol (26.6 g, 98% pure) of 4-ethoxyphenyldimethylsilane was added over a period of 30 minutes. An exothermal increase to 115° C. was observed. This renders the catalyst black. 40.4 g of product (GC: 94.3% pure) were then distilled off in a high vacuum at 180°–184° C. and 1 mbar. This corresponds to a yield of 79.3% of theory.

The following example was carried out analogously:

| Comparative Examples | Initial temperature °C. | Exothermal increase to [°C.] | Product yield % of theory |
|---|---|---|---|
| 12 | 100 | 155 | 78.2 |

Example 13

(Comparative example)

70 ml of n-heptane are initially introduced at reflux. One mol of 4-fluoro-3-chloroallylbenzene (172.7 g, 98.7% pure) plus 4 drops of a 30% solution of $H_2FtCl_6$ in isopropanol and 1 mol of 4-ethoxyphenyldimethylsilane (182.4 g, 98.6% pure) were added over a period of 1 hour.

An exothermic reaction sets in, giving an internal temperature of 130° C. 65.3% =0.751 mol of 4-ethoxyphenyl-3-(4-fluoro-3-chlorophenyl)propyldimethylsilane were detected in the heptane solution. This corresponds to a yield of 75.1% of theory.

Example 14

(Comparative example)

0.3 mol of 4-fluoro-3-chloroallylbenzene (51.6 g, 99.2% pure) and 0.3 mol of 4-ethoxyphenyldimethylsilane (56 g, 96.5% pure) are mixed and metered into a mixture of 25 ml of heptane and 2 drops of hexachloroplatinic acid (30% in isopropanol), which had also been initially introduced at 100° C., at 100° C. over a period of 25 minutes. Stirring is continued for 1 hour, giving a product mixture which, according to GC, contains 61.3% ($\triangleq$72.1% of theory) of 4-ethoxyphenyl-[3-(4-fluoro-3-chlorophenyl)propyl]dimethylsilane, 2.1% of 4-fluoro-3-chloroallylbenzene ($\triangleq$5.1% of the materials used) and 2.8% of 4-ethoxyphenyldimethylsilane ($\triangleq$6.4% of the materials used). In addition, substantial amounts of byproducts, for example 4-fluoro-3-chloro-ω-methylstyrenes (11.6% by GC =28.0% of the materials used.)

Example 15

Comparative example)

0.3 mol of 4-fluoro-3-chloroallylbenzene (51.6 g, 99.2% pure) and 0.3 mol of 4-ethoxyphenyldimethylsilane (56 g, 96.5% pure) are mixed and metered into a mixture of 10 g (96% pure) of 4-ethoxyphenyl[3-(4-fluoro-3-chlorophenyl)propyl]dimethylsilane ≙0.028 mol) and 2 drops of hexachloroplatinic acid (30% in isopropanol, which had also been initially introduced at 100° C., at 100° C. over a period of 20 minutes. Stirring is continued for 1 hour, giving a product mixture, which, according to GC, contains 59.9% of 4-ethoxyphenyl-[3-(3-chloro-4-fluorophenyl)propyl]dimethylsilane (≙57.6% of theory), 1.3% of 4-fluoro-3-chloroallylbenzene (≙2.9% of the materials used) and 2.6% of 4-ethoxyphenyldimethylsilane (≙5.7% of the materials used). In addition, substantial amounts of 4-fluoro-3-chloro-ω-methylstyrene (together 10.7% by GC ≙to 24.6% of theory) and other byproducts are detected.

I claim:

1. A process for the preparation of compounds of the formula I

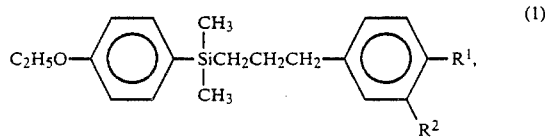

in which
R$^1$ is hydrogen, halogen, (C$_1$-C$_4$)alkyl, (C$_1$-C$_4$)alkoxy and
R$^2$ is hydrogen, halogen, (C$_1$-C$_4$)alkoxy or phenoxy, which may be substituted by halogen, (C$_1$-C$_4$)alkyl, (C$_1$-C$_4$)alkoxy or (C$_1$-C$_4$)alkylthio, by reaction of a compound of the formula II

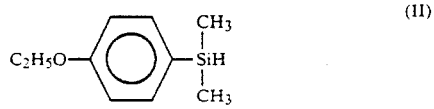

with a compound of the formula III

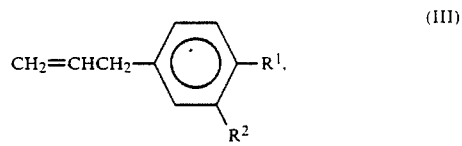

in which R$^1$ and R$^2$ have the meanings as in formula I, in the presence of catalytically active amounts of hexachloroplatinic acid, which comprises metering the starting compounds of the formulae II and III simultaneously into the reaction vessel at temperatures of 60° C. to 150° C. and allowing the reaction to go to completion.

2. The process as claimed in claim 1, wherein the starting compounds of the formulae II and III are metered simultaneously into the reaction vessel at temperatures of between 80° C. and 130° C.

3. The process as claimed in claim 1, wherein the catalyst, hexachloroplatinic acid, is dissolved in the compound of the formula III and this mixture is metered simultaneously with the compound of the formula II into the reaction vessel.

* * * * *